United States Patent
Lutz et al.

(10) Patent No.: US 11,167,078 B2
(45) Date of Patent: Nov. 9, 2021

(54) DEVICE AND METHOD FOR TEMPERING THE FLOW OF LIQUIDS IN MEDICAL DEVICES

(71) Applicant: W.O.M. WORLD OF MEDICINE GMBH, Berlin (DE)

(72) Inventors: Andreas Lutz, Berlin (DE); Karl-Heinz Guenter Schoenborn, Berlin (DE)

(73) Assignee: W.O.M. WORLD OF MEDICINE GMBH, Berlin (DE)

( * ) Notice: Subject to any disclaimer, the term of this patent is extended or adjusted under 35 U.S.C. 154(b) by 142 days.

(21) Appl. No.: 16/321,259

(22) PCT Filed: Jul. 20, 2017

(86) PCT No.: PCT/DE2017/000215
§ 371 (c)(1),
(2) Date: Jan. 28, 2019

(87) PCT Pub. No.: WO2018/019317
PCT Pub. Date: Feb. 1, 2018

(65) Prior Publication Data
US 2019/0231966 A1    Aug. 1, 2019

(30) Foreign Application Priority Data
Jul. 29, 2016  (DE) .......................... 102016009173.8

(51) Int. Cl.
*A61M 3/02*  (2006.01)
*F28F 3/12*  (2006.01)
(Continued)

(52) U.S. Cl.
CPC ............. *A61M 3/022* (2014.02); *A61B 1/128* (2013.01); *A61M 3/02* (2013.01); *F28F 3/12* (2013.01); *F28F 27/02* (2013.01); *A61M 2205/122* (2013.01); *A61M 2205/127* (2013.01); *A61M 2205/128* (2013.01); *A61M 2205/3334* (2013.01); *A61M 2205/3368* (2013.01); *A61M 2205/3606* (2013.01); *A61M 2205/366* (2013.01); *A61M 2205/3653* (2013.01); *A61M 2205/6027* (2013.01); *A61M 2206/14* (2013.01);
(Continued)

(58) Field of Classification Search
CPC ............ A61B 1/128; A61M 2205/122; A61M 2205/127; A61M 2205/128; A61M 2205/3334; A61M 2205/3368; A61M 2205/3606; A61M 2205/3653; A61M 2205/366; A61M 2205/6027; A61M 2206/14; F28D 2021/0019; F28D 2021/005; F28F 2250/06; F28F 2255/02; F28F 27/02; F28F 3/12
See application file for complete search history.

(56) References Cited

U.S. PATENT DOCUMENTS

2002/0045851 A1 *  4/2002  Suzuki .................... A61M 5/44
                                                            604/28
2013/0165848 A1    6/2013  Sebesta

FOREIGN PATENT DOCUMENTS

DE        102010036295 A1    3/2012

* cited by examiner

*Primary Examiner* — Deanna K Hall
(74) *Attorney, Agent, or Firm* — Stuart H. Mayer; Mayer & Williams PC

(57) ABSTRACT

The present invention relates to an apparatus for flow tempering medical irrigation fluids and to a method carried out with the aid of this apparatus.

15 Claims, 4 Drawing Sheets

(51) Int. Cl.
*F28F 27/02* (2006.01)
*A61B 1/12* (2006.01)
*F28D 21/00* (2006.01)

(52) U.S. Cl.
CPC .................. *F28D 2021/005* (2013.01); *F28D 2021/0019* (2013.01); *F28F 2250/06* (2013.01); *F28F 2255/02* (2013.01)

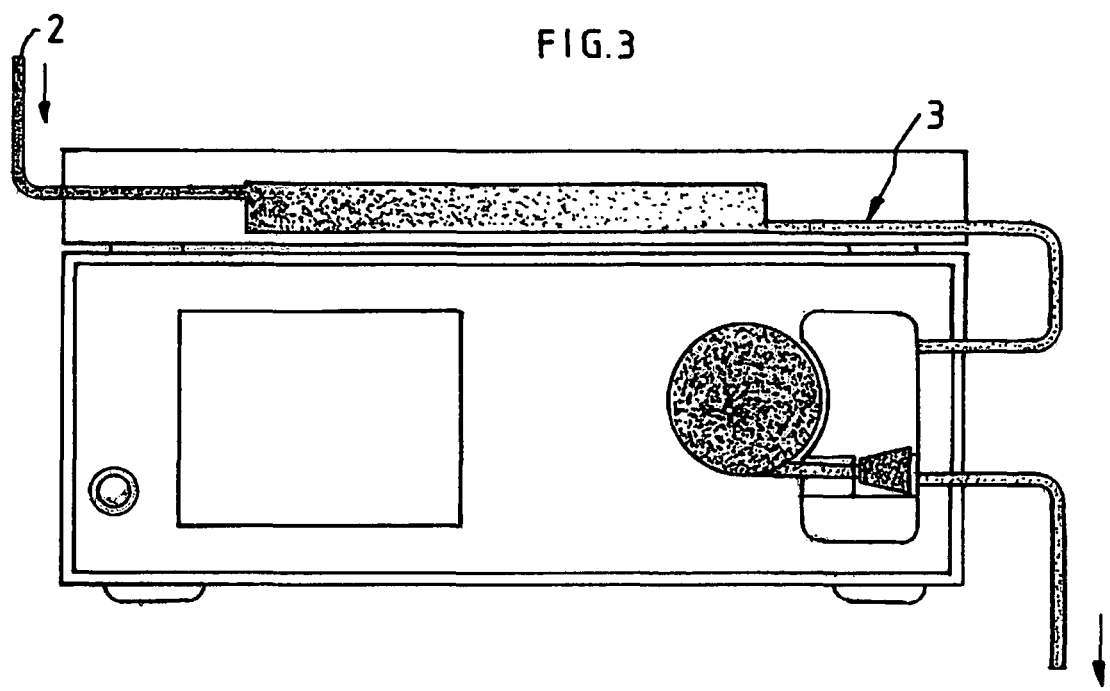
FIG.3
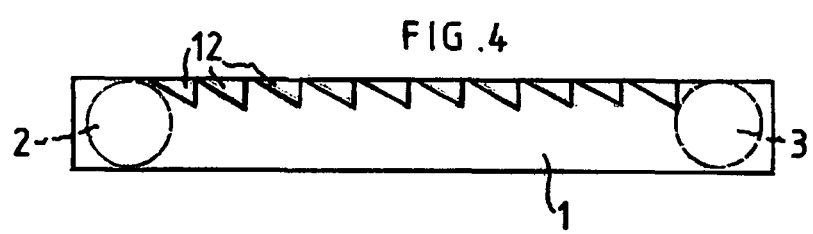
FIG.4
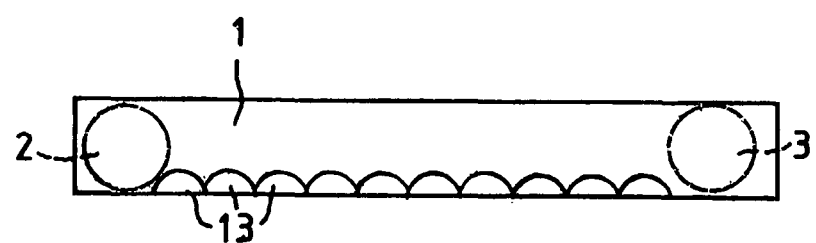

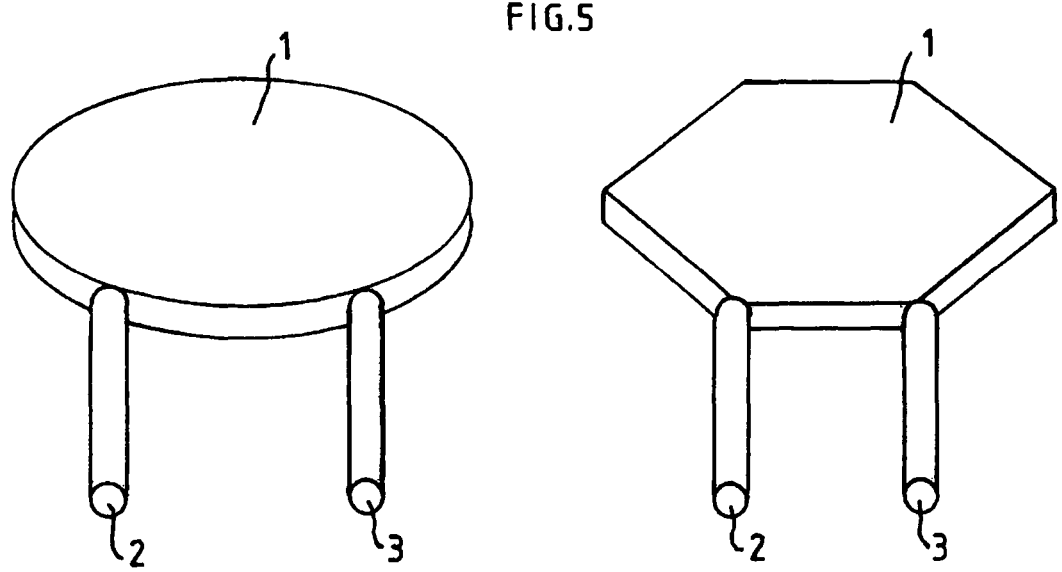
FIG.5
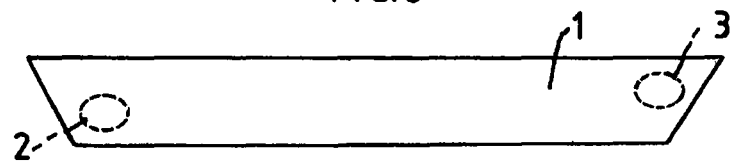
FIG.6
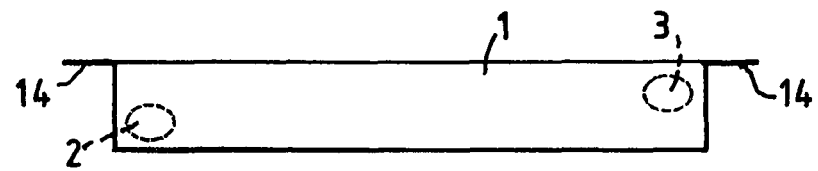

DEVICE AND METHOD FOR TEMPERING THE FLOW OF LIQUIDS IN MEDICAL DEVICES

BACKGROUND OF THE INVENTION

It is well known, in the context of most various medical methods of endoscopy, e.g., arthroscopy, (endo-) urology or hysteroscopy, to irrigate body cavities. Herein, usually, an irrigation fluid is pumped into a body cavity by means of a pump, e.g., a roller pump. It has proved advantageous to adapt the irrigation fluid, during application, to the body temperature, in order—for instance, in (endo-)urology and hysteroscopy—to avoid a local hypothermia of the patient's body. In prior art, different solutions are known (e.g., U.S. Pat. Nos. 6,480,257, 8,790,303, 7,153,285, US 2003/0216689 A1) that have different drawbacks, however. In arthroscopy it may be advantageous to cool the joint by the irrigation fluid, in order to reduce inflammatory processes, to avoid bleeding, and/or during surgery, to reduce the local metabolism.

Subject matter of the present invention is a novel apparatus that overcomes the various drawbacks of prior art.

Subject matter of the present invention, therefore, is an apparatus for flow tempering medical irrigation fluids, comprising
a heat exchanger body having at least one inlet and one outlet, with a respective hose connection,
wherein the heat exchanger body forms, by its heat exchanger body walls, a closed cavity,
wherein at least one heat exchanger body wall allows a good heat transfer (thermal conductance>1 W/(cm²K)),
wherein the heat exchanger body comprises two flow paths, one flow path having no thermal contact to the tempering element ("by-pass"), the heat exchanger body walls, at least locally, being reversibly deformable, so that, depending on the deformation, the flow paths are controllable,
further comprising at least one planar tempering element matching the heat exchanger body,
wherein the planar tempering element is integrated in a housing having an opening,
wherein, in the operating position, the heat exchanger body wall has contact with a good heat transfer to the planar tempering element, according to claim 1.

SUMMARY OF THE INVENTION

Advantageous embodiments of the invention will be explained in the following and are subject matter of the sub-claims.

The apparatus according to the invention consists, therefore, of a heat exchanger body, e.g., in the form a cartridge that is passed by the fluid to be tempered, and a planar tempering element adapted to the shape of the heat exchanger body.

In the preferred embodiment of the invention, the fluid to be tempered is heated from room temperature to body temperature, e.g., from 20° C. to 37° C. In this case, the planar tempering element is configured as a surface heating element.

In an alternative embodiment of the invention, the fluid to be tempered is cooled down from room temperature, e.g., of 20° C. to 3-5° C. In this case, the planar tempering element is configured as a surface cooling element. This alternative embodiment is explained below in more detail.

The heat exchanger body may have different geometric shapes. As illustrated in the enclosed figures, a preferred embodiment is the shape of a flat cuboid. The interior of the cuboid is substantially hollow and can receive irrigation fluid. The cuboid has at one location an inlet, at another location an outlet. Inlet and outlet may, as shown in FIG. 2, be arranged at a cuboid face. By supplying fluid into the inlet, the heat exchanger body is filled with the fluid, until it leaves again through the outlet. Preferably, in the operating position, the outlet is located at a higher level than the inlet, so that the originally included air can more easily escape. Alternatively, the heat exchanger body may have other geometric shapes, such as round, oval, hexagonal, octagonal, etc.

The heat exchanger body is preferably made of plastic (e.g., polycarbonate (PC), polyethylene terephthalate (PET), polyethylene terephthalate-glycol (PETG), polyvinyl chloride (PVC), polypropylene (PP), polyethylene (PE) or mixtures of these plastic materials. The plastic materials may also be filled with ceramic powder. Further, it is possible to make the heat exchanger body of metal, in particular of metal foils (e.g., aluminum foil). The individual components of the heat exchanger body may also be made of different materials. At least one heat exchanger body wall is made such that a good heat transfer is ensured. The thermal conductance of this wall (heat conducting wall) should at least be 1 W/(cm²K), preferably greater that 2.5 W/(cm²K).

With "heat transfer coefficient α" is meant the coefficient that describes the heat transfer (P=ΔQ/Δt) per unit area (P=ΔQ/Δt) over an interface according to the following equation:

$$P = \alpha \cdot \Delta A \cdot \Delta T$$

For this purpose, generally, all heat-conducting materials are suitable. Preferably, a metal foil, particularly preferably an aluminum foil is used. Alternatively, a plastic material filled with ceramic powder may be employed. Advantageously, the largest surfaces of the heat exchanger body are used for the heat transfer, e.g., the top surface or the bottom surface of a flat cuboid. In special embodiments, several surfaces may be designed in this way, e.g., the top surface and the bottom surface of a cuboid heat exchanger body.

According to the invention, the heat exchanger body comprises two flow paths: Most of the heat exchanger body will be heated by the heating element, while simultaneously the possibility of a "by-pass" is given, through which the fluid can directly flow from the inlet to the outlet, without being heated. The by-pass may be formed by corresponding shaping of the bottom of the heat exchanger body within the heat exchanger body, as it is shown, for example, in FIG. 2. Alternatively, the by-pass may be formed outside of the heat exchanger body, for instance, by a hose that extends in parallel to the heat exchanger body. In either case of this embodiment, actuators, for instance, valves (e.g., in the form of pinch valves) are provided that conduct the fluid flow either into the main chamber or into the by-pass. Preferably, the by-pass extends within the heat exchanger body through a section that has no contact to the surface planar tempering element described below (see FIG. 2). This embodiment allows to quickly and effectively control the outlet temperature of the irrigation fluid, in particular in applications, where the flow is very irregular. If in this case, e.g., due to a temporary blocking of the flow, the fluid temperature in the chamber should become too high, unheated irrigation fluid can specifically be added through the by-pass, in order to keep the outlet temperature constant. Further, this can be used to obtain a sufficient control speed of the outlet temperature, which will even with strong variations of the flow rate ensure a safe temperature adjustment.

In order to be able to control the fluid flow through heat exchanger body and by-pass, parts of the heat exchanger body are made of a resilient material (e.g., silicon), in order to control, by means of actuators integrated in the housing of the heating system, the fluid flow through the heat exchanger body and the by-pass (in the way of a pinch valve). Depending on the used wall material, a local thickness reduction or shaping of the material (e.g., in the way of a bellow) may already be sufficient to ensure the required flexibility in the meaning of a reversible deformability. Preferably, the actuators are arranged such that, in the position of rest, in the case of failures or disorders, the fluid will pass through the by-pass and not through the heating path. In this way, it is secured that in no case the fluid will be supplied to the patient in a too hot condition.

The heat exchanger body described further above is used, according to the invention, together with a correspondingly adapted tempering element, e.g., a heating element. The heating element is shaped such that at least one wall of the heat exchanger body can be heated over its surface. Such heating elements in the form of planar heating foils are commercially available and in most cases consist of a one-layer and flatly arranged ohmic heating coil that is embedded in an insulating plastic film, for instance, of silicon or polyimide (trade name Kapton®)

Alternatively, the heating element may also be configured as a heating surface with a wire-shaped heating conductor that is compressed in ceramic powder (=electric insulation), which in turn is enclosed in a metallic outer sleeve/housing.

In tight thermal contact to the heating element, e.g., the heating foil, temperature transducers may be arranged at one or several locations, in order to be able to control the temperature of the heating foil.

As a special embodiment, this heating foil may also be made of a PTC element that experiences an increase in electrical resistance when its temperature is raised. In this way, under certain circumstances, the temperature control may not be needed, since the increasing resistance when the temperature is raised will cause a decrease of the heating power. Such PTC elements and the respective controls are state of the art and need not be explained here in more detail.

Reasonably, the heating element is disposed in the interior of a housing that may have practically any outside shape. Crucial for the use according to the invention is an opening in the housing for receiving the described heat exchanger body, e.g., in the form of a slot. The opening is, of course, designed in its geometry such that the heat exchanger body can be introduced into the opening. At a side of the cavity accessible through the opening, e.g., the lower side, there is positioned the planar heating element, e.g., in the form a heating foil. The heat exchanger body described above has to be introduced into the opening in such a way that the side that ensures the heat transfer comes into contact with the heating element. By adjustment of the heating power, the temperature of the irrigation fluid can be controlled.

As has been found out, the heat exchanger body is preferably heated from below. Due to the thermal convection, a thermal mixing of the fluid will occur in the heat exchanger body. In the case of the mode of operation described further below, where the fluid is cooled down, the cooling element is preferably arranged at top. Since, in principle, two walls of the heat exchanger body may also be formed of heat-conducting material, e.g., the bottom face and the top face, heating or cooling may also be performed from two sides.

In another embodiment of the invention, it is possible to provide a heating surface as well as a cooling surface in the housing. Depending on the setting of the apparatus, thus, alternatively heating or cooling can be carried out.

Preferably, the geometric shape of the said introduction opening is designed such that a mispositioning of the heat exchanger body can be excluded as far as possible. For this purpose, complementing symbols or color codes may be helpful.

The apparatus according to the invention can be operated as follows:

From a storage container with medical irrigation fluid, a hose extends to the inlet of the heat exchanger body. Another hose connects the outlet of the heat exchanger body to the inlet of a medical pump, e.g., a roller pump. From the outlet of the pump, another hose is guided to a medical instrument, such as an endoscope. Alternatively, the device according to the invention may also operated without a pump in pure gravitation supply; in this case, the hose at the outlet extends directly from the heat exchanger body to the instrument, with all other features according to the invention remaining unchanged. The heat exchanger body is introduced into the heating device. The fluid preheated by the heating device according to the invention to the desired temperature (e.g., the patient's body temperature) is supplied by means of the irrigation pump into the patient's body.

In the following, preferred embodiments of the invention will be described:

The heat exchanger body preferably is configured as a disposable article and is, therefore, disposed of after a single use. The heat exchanger body preferably consists of plastic (e.g., polycarbonate (PC), polyethylene terephthalate (PET), polyethylene terephthalate-glycol (PETG), polyvinyl chloride (PVC), polypropylene (PP), polyethylene (PE) or mixtures of these plastic materials), which is produced by deep drawing. Alternatively, of course, other techniques may also be considered, such as, injection molding or 3D printing. In this way, the top side of the heat exchanger body may simply be coated with a glued or welded aluminum foil (thickness, e.g., 20-90 μm, preferably 60 μm). In a preferred embodiment, the aluminum foil is coated, on the side that forms the inner side of the heat exchanger body, with a plastic layer (e.g., 1-5 μm, preferably 2 μm polypropylene). In this way, a direct contact of the fluid with aluminum is prevented, without impairing the required heat transfer.

In order to be able to transmit the required heating power, the base surface area of the heat exchanger body is in general between 100 and 1,600 $cm^2$ (e.g., 10×10 cm to 40×40 cm).

The hose connections are, for instance, injection-molded parts or other plastic shaped parts and are preferably made of the same plastic material as the base part of the heat exchanger body. The hose connections are respectively inserted into correspondingly prepared openings and are welded or glued to the heat exchanger body. Alternatively, the hose connections may also directly be formed by deep drawing, extrusion, or 3D printing.

The heat exchanger body is preferably flat with a height of 5-20 mm. The opening in the housing is configured in a manner adapted thereto. Preferably, the housing opening is dimensioned such that operating personnel cannot introduce fingers into the opening, in order to avoid accidents by burns.

Furthermore, by corresponding shaping of heat exchanger body and opening in the housing, it can be ensured that the heat exchanger body is placed in the proper manner into the housing, e.g., by a slight trapezoidal deviation of the cuboid shape (FIG. 6 top) with corresponding shaping of the opening in the housing or by adding guide rails to the side of the heat exchanger body (FIG. 6 bottom) with corresponding guide slots in the housing. Alternatively or complementarily, symbols or color codes provided on heat exchanger body and housing can exclude faulty operations.

Further preferably, the tempering apparatus includes a temperature sensor for checking the outlet temperature of the irrigation fluid. For this purpose, for instance, a temperature sensor may be integrated in the outlet of the heat exchanger body.

As has been found, when using an aluminum foil for the heat transfer, the heat conduction of this foil is so good that the temperature measurement by a contact thermometer that is positioned close to the outlet of the heat exchanger body, is sufficient to measure the temperature precisely enough. In this way, the temperature sensor can be a component of the housing and can be re-used.

In an improvement of the described invention, the housing includes a pump of negative pressure. The generation of a negative pressure on the side of the heat transition allows to press the heat exchanger body onto the tempering element, so that the heat transfer is improved. The inlet connector or inlet connectors of the pump will be located in the area of the heating element. It is recommended that around the planar heating element, a sealing material (e.g., a silicon seal in the form of a peripheral sealing cord) is provided, in order that the negative pressure can easily be maintained. In this embodiment of the invention, a pressure between heat exchanger body and heating or cooling surface of 0.05 to 0.3 bar (0.7 to 4.4 psi) is intended, preferred is approx. 0.1 bar (1.5 psi). With this pressure, the heat-conducting wall of the heat exchanger body (e.g., the aluminum foil) is attracted to less than 1 μm to the heating or cooling surface. Simultaneously, with a pressure of 0.05 to 0.3 bar (0.7 to 4.4 psi), an excellent heat transfer is obtained.

In another embodiment of the invention, one or several inner sides of the heat exchanger inner walls comprise a structure, e.g., in the form a wave-shaped, saw-tooth or herringbone configuration of the inner faces (FIG. 4). It has been found that such a structure contributes to a turbulence of the passing fluid and thus to a thermal homogenization of the flow and the temperature of the heat exchanger body. A structure of that inner wall that is opposite to the wall with heat transfer has proved to be particularly advantageous.

Depending on the size of the heat exchanger body and the elasticity of the side of the heat exchanger material, support elements may also be arranged in the interior (e.g., of cylindrical shape), to prevent a collapse of the heat exchanger body. The heat exchanger body walls may also comprise stiffening devices (e.g., ribs).

It is recommendable that the planar heating element of the heating device achieves a maximum temperature that is slightly higher than the patient's body temperature (e.g., 39° C.). For safety reasons, the temperature of the planar heating element is monitored by corresponding temperature sensors. Further, the outlet temperature of the irrigation fluid from the heat exchanger body is monitored by a temperature sensor. The latter may be, as mentioned above, a component of the heat exchanger body. For cost reasons, it is recommended to integrate the temperature sensor in the heating device, e.g., in the form of a contact sensor measuring the temperature of the surface of the aluminum foil.

It has been found that for optimization of the temper control, it is advantageous to measure the flow through the heat exchanger body. When the apparatus according to the invention is operated in combination with a pump, e.g., a medical roller pump, then it is sufficient, in general, to determine the flow rate of the pump. When the flow rate is not determined otherwise and is available, the apparatus according to the invention may also be prepared for simultaneous flow measurement. The flow measurement may, for instance, be made following the Venturi principle. For this purpose, the flow cross-section has to be narrowed, for instance, in the area of the fluid entry or exit. By measuring the differential pressure (in the constriction and behind the constriction), the flow can be determined. For measuring the pressure, corresponding sensors are required. The pressure sensors may directly be integrated in the heat exchanger body, i.e. in its inlet or outlet, respectively. Alternatively, a flexible membrane may be arranged at the measuring points, the deflection of which is used for pressure measurement by corresponding pressure transducers in the housing.

Alternatively, the flow rate may also be measured thermally: For this purpose, at a suitable location of the heat exchanger body, e.g., in the area of the fluid inlet or outlet, respectively, a temperature sensor has to be disposed. In immediate proximity of the temperature sensor, a heating element, e.g., a resistance heating arrangement, needs to be provided. The heating element may heat continuously or discontinuously, with the heating power being determined. The achieved temperature increase in the environment of the heating element, which is measured by the temperature sensor, is a measure for the flow rate. With high flow rate, no noteworthy temperature increase will be obtained, while with low flow rate, a temperature increase is measured by the thermometer. The advantage of this kind of the flow measurement is that the heating element, as well as the temperature sensor need not be components of the heat exchanger body, but can initiate the measurement by contact to the surface of the heat exchanger body. In this way, the heat exchanger body can be produced in a most simple and thus most economic way.

The apparatus according to the invention is able to heat up to 800 ml/min aqueous irrigation fluid from room temperature (20° C.) to 38° C.

The apparatus according to the invention has a series of advantages over prior art. First, the apparatus according to the invention can simply be integrated in the existing medical equipment. The apparatus can be used as a complement to existing pump systems (e.g., a roller pump) that can further be operated in a usual way. Alternatively, the apparatus according to the invention may also be used as a "stand-alone" solution. In this case, the fluid flows from a higher level storage container solely by gravity ("gravity supply") through the heat exchanger body to the medical instrument, e.g., endoscope.

By using the disposable heat exchanger body, the required safety, in particular the sterility, can be ensured in a simple way. The manufacturing costs of the heat exchanger body are relatively low.

Further, by the apparatus according to the invention, only that part of the irrigation fluid is heated that is also immediately to be consumed. The apparatus according to the invention thus avoids that, for instance, the entire irrigation fluid storage container has to be heated, what would have a negative impact on the stability of the solution.

In particular, the embodiment with integrated by-pass also enables a highly precise control of the fluid temperature even with heavily alternating fluid flow.

As already mentioned above, the apparatus according to the invention may also be used for flow-through cooling. Such cooling systems are advantageous, for instance, for use in arthroscopy, in order to minimize swelling, bleeding, and experiencing pain by the patient. For this purpose, the irrigation fluid may be cooled down to a few degrees above the freezing point (e.g., 1-10° C., preferably 2-5° C.). In this embodiment of the invention, instead of a planar heating element, a planar cooling element is used. This may be a planar compressor-driven cooler. Alternatively, a cooling agent may also be used for cooling. In another embodiment of the invention, a Peltier element may also be used. In the embodiment with such a Peltier element, by reversal of the flow direction (changing poles), cooling as well as heating can be achieved.

As already mentioned further above, cooling of the heat exchanger body is preferably made from above. Of course, it is also possible to cool multiple sides, e.g., base face and top face of a cuboid heat exchanger body. The further alternative embodiments of the invention explained above may be used in a completely analogous manner in the embodiment with cooling, as for instance, the temperature measurement and/or the flow measurement. Implementing a "by-pass" is possible in an analogous manner, in order to admix irrigation fluid at room temperature, if required.

In another possible embodiment of the invention, the heat exchanger body may also be heated and cooled from two different sides (e.g., bottom face and top face).

It is, for instance, imaginable to provide the housing on one side (e.g., the bottom side) with a heating element, and on another side (e.g., the top side) with a cooling element. When using a heat exchanger body with two heat-conducting walls, then, depending on the mode of operation, cooling or heating can be performed. Under certain circumstances, it may even be suitable to operate a device according to the invention with the ability of cooling and heating, in order to be able to control the fluid temperature more rapidly, effectively, and/or precisely.

BRIEF DESCRIPTION OF THE DRAWINGS

FIG. 3 schematically shows the use of the apparatus.

FIG. 4 shows a cross-section of a heat exchanger body with a saw tooth-type configuration of the top face (top) or a wave-shaped of the bottom face (bottom).

FIG. 5 shows a cross-section of a heat exchanger body with a trapezoidal shape (top) or integrally formed guide rails (bottom), respectively.

FIG. 6 shows heat exchanger bodies having different geometries, such as round (top) or hexagonal (bottom).

EXPLANATION OF THE FIGURES

Figure 1:
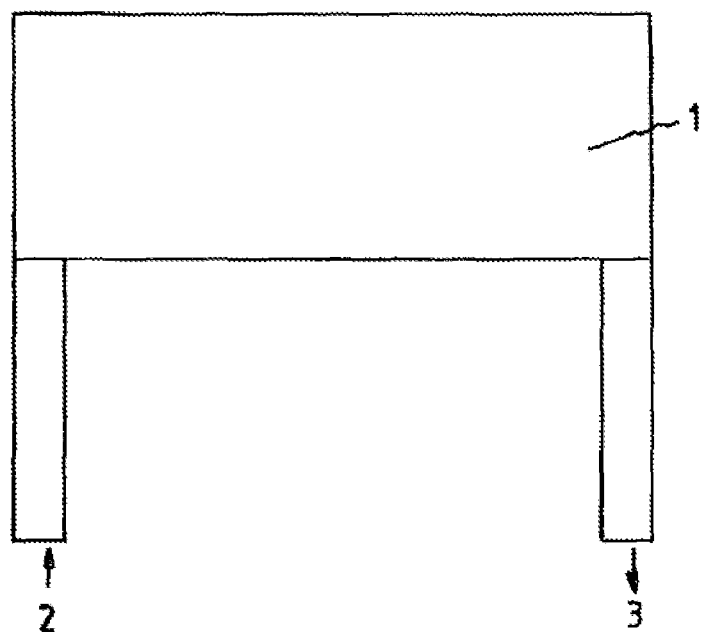
FIG. 1 shows the basic form of a heat exchanger body (1) according to the invention in a top view (top) and a perspective view (bottom).

FIG. 1 shows the basic form of a heat exchanger body (1) according to the invention in a top view (top) and a perspective view (bottom). The heat exchanger housing is substantially cuboid, with two connections as inlet (2) or outlet (3), respectively, being shown.

Figure 2:
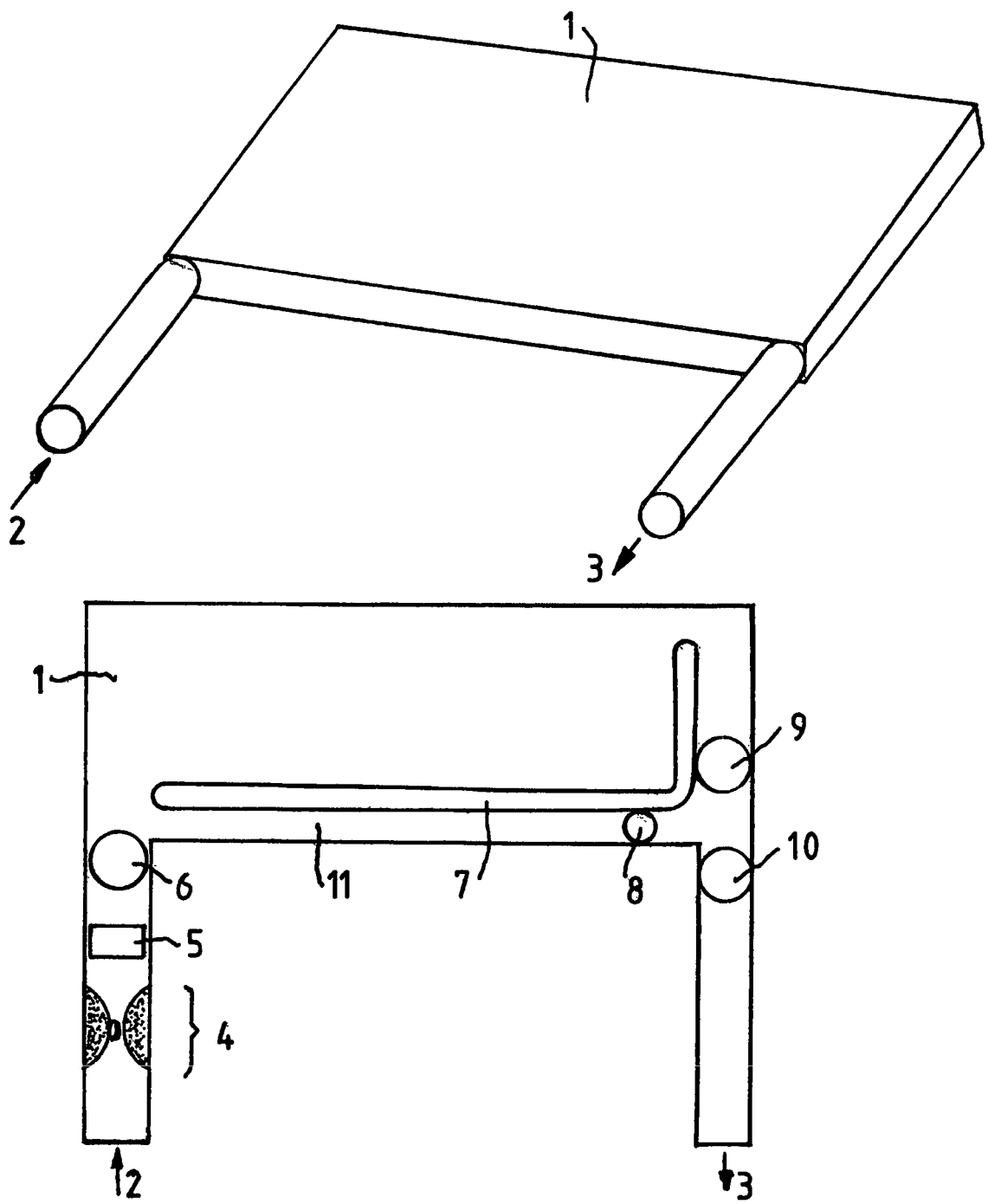
FIG. 2 shows an embodiment of the heat exchanger body with a by-pass.

FIG. 2 shows a special embodiment of the heat exchanger body (1) with a by-pass (11). The by-pass is separated, within the body, by a separating wall (7) from the remainder of the volume. The heat exchanger body comprises at least at two locations deformable elements (8, 9) that control, in the manner of a pinch valve, the flow through the main portion or the by-pass, respectively. In addition, temperature sensors are provided that measure the temperature of the inlets (6) or of the outlets (10), respectively. Further, a flow meter of the Venturi type is shown: For this purpose, a constriction (4) is formed in the inlet. Pressure sensors in or behind (5) the constriction allow the calculation of the fluid flow by determining the differential pressure.

FIG. 3 schematically shows the use of the apparatus according to the invention:

The fluid reservoir is supplied by means of a hose into the heat exchanger body, which is disposed in the housing with the planar heating device. At the outlet of the heat exchanger body, another hose is connected that leads to the roller pump. At the outlet of the roller pump there are instruments leading to the patient. The figure clearly shows that the apparatus according to the invention is suitable in a simple manner as a complement to the existing medical equipment.

FIG. 4 shows a cross-section of a heat exchanger body with a saw tooth-type configuration of the top face (top) or a wave-shaped of the bottom face (bottom). The flow through such a heat exchanger body will lead to a turbulence of the fluid with the consequence of a better heat transfer.

FIG. 5 shows a cross-section of a heat exchanger body with a trapezoidal shape (top) or integrally formed guide rails (14) (bottom), respectively. In combination with the complementarily designed opening in the housing, faulty insertions can reliably be prevented.

FIG. 6 shows heat exchanger bodies having different geometries, such as round (top) or hexagonal (bottom).

The invention claimed is:

1. An apparatus for flow tempering medical irrigation fluids, comprising
   a heat exchanger body having at least one inlet and one outlet, with a respective hose connection,
   wherein the heat exchanger body forms, by its heat exchanger body walls, a closed cavity,
   wherein at least one heat exchanger body wall allows a good heat transfer,
   wherein the heat exchanger body comprises two flow paths, one flow path having no thermal contact to the tempering element by shaping the bottom of the heat exchanger body, the heat exchanger body walls, at least locally, being reversibly deformable, so that, depending on the deformation, the flow paths are controllable so that untempered irrigation fluid can specifically be added through the flow path having no thermal contact to the tempering element,
   further comprising at least one planar tempering element matching the heat exchanger body,
   wherein the planar tempering element is integrated in a housing having an opening,
   wherein, in the operating position, the heat exchanger body wall has contact with a good heat transfer to the planar tempering element.

2. The apparatus of claim 1, wherein a substantially cuboid shape of the heat exchanger body.

3. The apparatus of claim 1, wherein the wall ensuring the heat transfer is formed by an aluminum foil.

4. The apparatus of claim 1, wherein the planar tempering element is formed by a heating foil.

5. The apparatus of claim 1, wherein the housing comprises at least one contact thermometer that rests, in the operating position of the apparatus, on the wall that ensures the heat transfer.

6. The apparatus of claim 1, wherein the housing comprises a vacuum pump that generates a negative pressure between heat exchanger body wall and tempering element.

7. The apparatus of claim 6, wherein the negative pressure between heat exchanger body wall and tempering element is 0.05 to 0.3 bar.

8. The apparatus of claim 1, wherein at least one heat exchanger body wall comprises a surface structure.

9. The apparatus of claim 1, wherein the heat exchanger body in the area of the inlet comprises a constriction of the flow cross-section, in the constriction and before the constriction one measuring point each for pressure measurement being provided.

10. The apparatus of claim 1, wherein the housing, in the area of the inlet or outlet of the heat exchanger body being in the operating position, comprises at least one sensor for thermal flow measurement, the sensor for thermal flow measurement including a heating element and a temperature sensor.

11. A method for flow tempering a fluid flow of a medical irrigation fluid, wherein a medical irrigation fluid is conducted through an apparatus with a heat exchanger body having at least one inlet and one outlet, with a respective hose connection,
wherein the heat exchanger body forms, by its heat exchanger body walls, a closed cavity,
wherein at least one heat exchanger body wall allows a good heat transfer,
wherein the heat exchanger body comprises two flow paths, one flow path having no thermal contact to the tempering element by shaping the bottom of the heat exchanger body, wherein the heat exchanger body walls, at least locally, being reversibly deformable, so that, depending on the deformation, the flow paths are controllable so that untempered irrigation fluid can specifically be added through the flow path having no thermal contact to the tempering element,
wherein the apparatus further comprises at least one planar tempering element matching the heat exchanger body,
wherein the planar tempering element is integrated in a housing having an opening, wherein, in the operating position, the heat exchanger body wall has contact with a good heat transfer to the planar tempering element, so that the medical irrigation fluid is tempered during the passage.

12. The apparatus of claim 1 wherein at least one heat exchanger body wall has a thermal conductance greater than 1 W/(cm2K).

13. The apparatus of claim 7, wherein said negative pressure between heat exchanger body wall and tempering element is 0.1 bar.

14. The apparatus of claim 1, wherein the heat exchanger body in the area of the outlet comprises a constriction of the flow cross-section, in the constriction and behind the constriction one measuring point each for pressure measurement being provided.

15. The apparatus of claim 1, wherein the housing, in the area of the inlet and outlet of the heat exchanger body being in the operating position, comprises at least one sensor for thermal flow measurement, the sensor for thermal flow measurement including a heating element and a temperature sensor.

* * * * *